United States Patent
Segawa (10) Patent No.: US 11,771,308 B2
(45) Date of Patent: Oct. 3, 2023

(54) MEDICAL CONTROL DEVICE AND MEDICAL OBSERVATION SYSTEM

(71) Applicant: Sony Olympus Medical Solutions Inc., Tokyo (JP)

(72) Inventor: Kazunori Segawa, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 17/519,593

(22) Filed: Nov. 5, 2021

(65) Prior Publication Data

US 2022/0151472 A1    May 19, 2022

(30) Foreign Application Priority Data

Nov. 13, 2020  (JP) ................... 2020-189817

(51) Int. Cl.
*A61B 1/00*    (2006.01)
*H04N 23/66*   (2023.01)
*H04N 23/50*   (2023.01)

(52) U.S. Cl.
CPC ...... *A61B 1/00188* (2013.01); *A61B 1/00006* (2013.01); *H04N 23/66* (2023.01); *H04N 23/555* (2023.01)

(58) Field of Classification Search
CPC ............ A61B 1/00006; A61B 1/00009; A61B 1/00188; H04N 23/555; H04N 23/60; H04N 23/66; H04N 23/673; H04N 23/71; H04N 23/73
See application file for complete search history.

(56) References Cited

U.S. PATENT DOCUMENTS

| | | | | |
|---|---|---|---|---|
| 4,801,792 A * | 1/1989 | Yamasita | ............... | G02B 5/005 250/205 |
| 5,315,383 A * | 5/1994 | Yabe | ................... | A61B 1/00105 348/72 |
| 6,425,858 B1 * | 7/2002 | Minami | ................... | H04N 23/69 348/240.99 |
| 7,173,770 B2 * | 2/2007 | Kashiki | .......... | G02B 15/143103 359/689 |
| 10,003,370 B2 * | 6/2018 | Fathollahi | ............. | H04M 1/185 |
| 2002/0055669 A1 * | 5/2002 | Konno | ................... | A61B 1/051 600/167 |
| 2007/0237514 A1 * | 10/2007 | Pillman | .............. | H04N 23/6815 396/153 |
| 2008/0007644 A1 * | 1/2008 | Matsumoto | .......... | H04N 23/665 348/E5.045 |

(Continued)

FOREIGN PATENT DOCUMENTS

JP         2019-33971 A      3/2019

*Primary Examiner* — Peter D Le
(74) *Attorney, Agent, or Firm* — XSENSUS LLP (57) ABSTRACT

A medical control device includes a focus controller configured to move a focus lens included in an imaging device configured to capture an object image taken in by an endoscope and generate a captured image, and control a focus position, wherein the focus controller is configured to executes remote shooting control for moving the focus lens and setting the focus position in a position of a hyperfocal distance corresponding to the endoscope in a case where an object distance from the endoscope to an object is included in a range of an object distance from the endoscope to the object at which remote shooting is performed.

12 Claims, 10 Drawing Sheets

(56) References Cited

U.S. PATENT DOCUMENTS

| | | | |
|---|---|---|---|
| 2008/0062261 A1* | 3/2008 | Sudo | A61B 1/00188 348/E5.045 |
| 2010/0292538 A1* | 11/2010 | Hirata | A61B 1/0669 600/129 |
| 2010/0309364 A1* | 12/2010 | Brunner | G03B 13/36 348/E5.045 |
| 2011/0292272 A1* | 12/2011 | Terashima | H04N 23/673 348/E5.045 |
| 2012/0197079 A1* | 8/2012 | Kuriyama | G02B 23/2476 600/109 |
| 2014/0039257 A1* | 2/2014 | Higuchi | A61B 1/00096 600/109 |
| 2014/0307072 A1* | 10/2014 | Takahashi | H04N 23/69 348/65 |
| 2015/0080651 A1* | 3/2015 | Azuma | A61B 1/00188 600/103 |
| 2015/0112128 A1* | 4/2015 | Yoshino | A61B 1/00188 600/103 |
| 2016/0000306 A1* | 1/2016 | Takayama | A61B 1/00126 600/109 |
| 2016/0128545 A1* | 5/2016 | Morita | A61B 1/00188 600/109 |
| 2017/0347989 A1* | 12/2017 | Ikuma | A61B 1/00 |
| 2018/0243043 A1* | 8/2018 | Michihata | A61B 1/00087 |
| 2018/0267291 A1* | 9/2018 | Mikami | G02B 3/14 |

* cited by examiner

MEDICAL CONTROL DEVICE AND MEDICAL OBSERVATION SYSTEM

CROSS-REFERENCE TO RELATED APPLICATION

This application claims priority from Japanese Application No. 2020-189817, filed on Nov. 13, 2020, the contents of which are incorporated by reference herein in its entirety.

BACKGROUND

The present disclosure relates to a medical control device and a medical observation system.

In the medical field, there has been known a medical observation system that observes the inside of a subject (inside a living body) (see, for example, JP 2019-33971 A).

The medical observation system described in JP 2019-33971 A includes an endoscope that takes in an object image in the organism from a distal end, an imaging device to which the endoscope is attached, the imaging device capturing the object image and generating a captured image, and a medical control device that controls the operation of the imaging device. A diaphragm that adjusts a light amount made incident on an image sensor is provided in the imaging device.

SUMMARY

Incidentally, in a configuration in which the diaphragm is provided in the imaging device as in the medical observation system described in JP 2019-33971 A, the medical control device may execute, for example, control explained below.

The medical control device changes a diaphragm value of the diaphragm in order to change brightness of an image in a specific detection region in an entire image region in the captured image to reference brightness.

In the control, in the case of proximity shooting in which an object distance (a working distance) from the distal end of the endoscope to the object is relatively small, the medical control device increases the diaphragm value (narrows the diaphragm) because the brightness of the image in the detection region in the captured image increases. That is, in the case of the proximity shooting, since the diaphragm value increases, it is possible to obtain a captured image having a large depth of field. On the other hand, in the case of a remote shooting in which the object distance is relatively large, the medical control device reduces a diaphragm value (opens the diaphragm) because the brightness of the image in the detection region in the captured image decreases. That is, in the case of the remote shooting, since the diaphragm value decreases, a captured image having a small depth of field is obtained.

Therefore, there has been a demand for a technique that may obtain a captured image having a large depth of field and suitable for observation even in the case of the remote shooting.

According to one aspect of the present disclosure, there is provided a medical control device including a focus controller configured to move a focus lens included in an imaging device configured to capture an object image taken in by an endoscope and generate a captured image, and control a focus position, wherein the focus controller is configured to executes remote shooting control for moving the focus lens and setting the focus position in a position of a hyperfocal distance corresponding to the endoscope in a case where an object distance from the endoscope to an object is included in a range of an object distance from the endoscope to the object at which remote shooting is performed.

DETAILED DESCRIPTION

Modes for carrying out the present disclosure (hereinafter, embodiments) are explained below with reference to the drawings. Note that the present disclosure is not limited by the embodiments explained below. Further, in the description of the drawings, the same portions are denoted by the same reference numerals and signs.

First Embodiment

Schematic Configuration of a Medical Observation System

Figure 1:
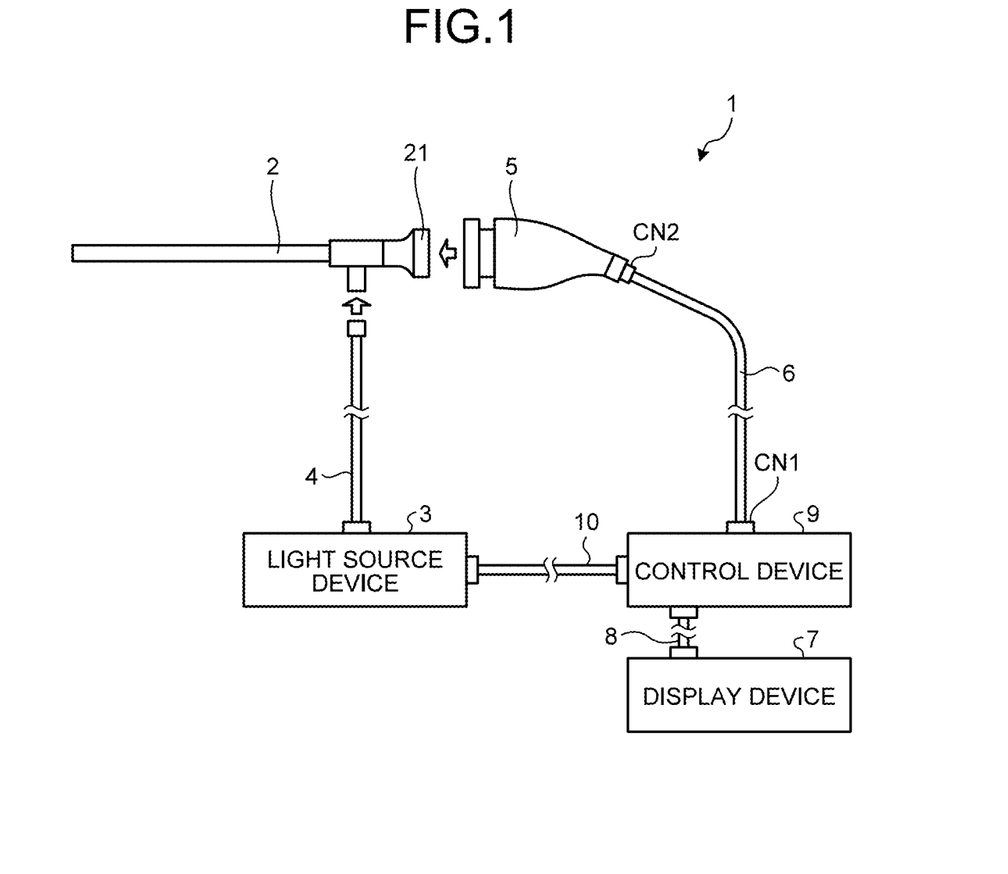
FIG. 1 is a diagram illustrating a medical observation system according to a first embodiment.
Figure 2:
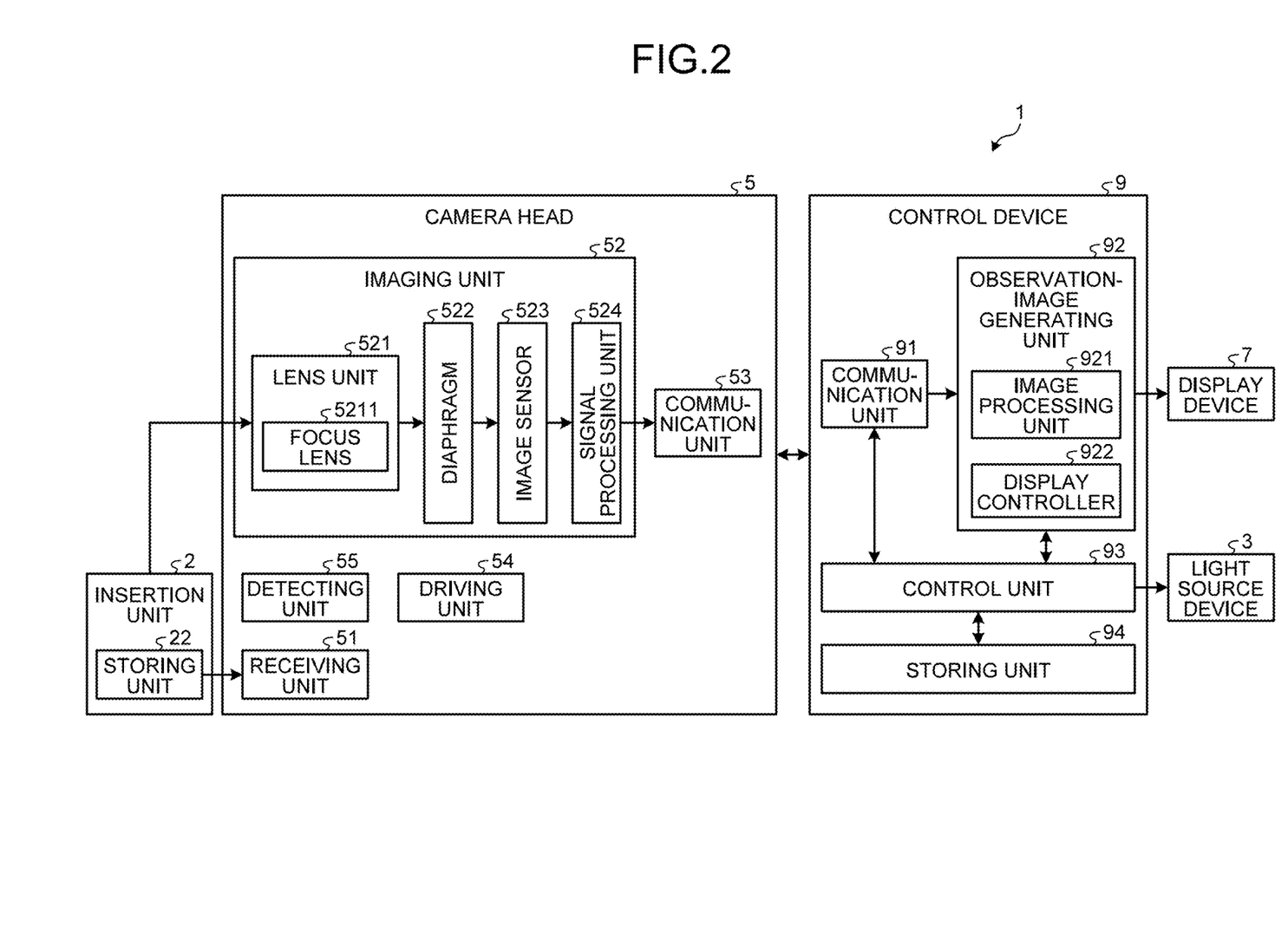
FIG. 2 is a block diagram illustrating the medical observation system.

FIG. 1 is a diagram illustrating a medical observation system 1 according to a first embodiment. FIG. 2 is a block diagram illustrating the medical observation system 1.

The medical observation system 1 is a system that is used in the medical field and observes the inside of an organism. The medical observation system 1 includes, as illustrated in FIG. 1, an insertion unit 2, a light source device 3, a light guide 4, a camera head 5, a first transmission cable 6, a display device 7, a second transmission cable 8, a control device 9, and a third transmission cable 10.

The insertion unit 2 is equivalent to the endoscope according to the present disclosure. In the first embodiment, the insertion unit 2 is configured by a rigid endoscope. That is, the insertion unit 2 has an elongated shape, the entirety of which is rigid or a part of which is soft and the other part of which is rigid, and is inserted into an organism. An optical system (not illustrated) that is configured using one or a plurality of lenses and condenses an object image is provided in the insertion unit 2. Further, a storing unit 22 (FIG. 2) that stores a scope ID (Identifier) for uniquely identifying a type of the insertion unit 2 is provided in an eyepiece unit 21 (FIG. 1) provided at the proximal end of the insertion unit 2. The scope ID is equivalent to the identification information according to the present disclosure.

One end of the light guide 4 is connected to the light source device 3. The light source device 3 supplies illumination light having a light amount designated by the control device 9 to the one end of the light guide 4 under control by the control device 9. Note that, in the first embodiment, the light source device 3 is configured separately from the control device 9. However, the light source device 3 is not limited to this. A configuration in which the light source device 3 is provided inside the control device 9 may be adopted.

The one end of the light guide 4 is detachably connected to the light source device 3 and the other end of the light guide 4 is detachably connected to the insertion unit 2. The light guide 4 transmits light supplied from the light source device 3 from the one end to the other end and supplies the light to the insertion unit 2. The light supplied to the insertion unit 2 is emitted from the distal end of the insertion unit 2 and radiated on the inside of the organism. The light (an object image) radiated on the inside of the organism and reflected on the inside of the organism is condensed by an optical system in the insertion unit 2.

The camera head 5 is equivalent to the imaging device according to the present disclosure. The camera head 5 is detachably connected to the eyepiece unit 21 in the insertion unit 2. The camera head 5 captures the object image condensed by the insertion unit 2 and generates a captured image under the control by the control device 9.

Note that a detailed configuration of the camera head 5 is explained below.

One end of the first transmission cable 6 is detachably connected to the control device 9 via a connector CN1 (FIG. 1) and the other end of the first transmission cable 6 is detachably connected to the camera head 5 via a connector CN2 (FIG. 1). The first transmission cable 6 transmits the captured image and the like output from the camera head 5 to the control device 9 and transmits each of a control signal, a synchronization signal, a clock, electric power, and the like output from the control device 9 to the camera head 5.

Note that, as the transmission of the captured image and the like from the camera head 5 to the control device 9 via the first transmission cable 6, the captured image and the like may be transmitted by an optical signal or may be transmitted by an electric signal. The same applies to the transmission of the control signal, the synchronization signal, and the clock from the control device 9 to the camera head 5 via the first transmission cable 6.

The display device 7 is configured by a display including liquid crystal, organic electro luminescence (EL), or the like and displays an image based on a video signal from the control device 9 under the control by the control device 9.

One end of the second transmission cable 8 is detachably connected to the display device 7 and the other end of the second transmission cable 8 is detachably connected to the control device 9. The second transmission cable 8 transmits the video signal processed by the control device 9 to the display device 7.

The control device 9 is equivalent to the medical control device according to the present disclosure. The control device 9 is configured by a central processing unit (CPU), a field-programmable gate array (FPGA), or the like and collectively controls the operations of the light source device 3, the camera head 5, and the display device 7.

Note that a detailed configuration of the control device 9 is explained below.

One end of the third transmission cable 10 is detachably connected to the light source device 3 and the other end of the third transmission cable 10 is detachably connected to the control device 9. The third transmission cable 10 transmits a control signal from the control device 9 to the light source device 3.

Configuration of the Camera Head

The configuration of the camera head 5 is explained with reference to FIG. 2.

The camera head 5 includes, as illustrated in FIG. 2, a receiving unit 51, an imaging unit 52, a communication unit 53, a driving unit 54, and a detecting unit 55.

When the camera head 5 is connected to the eyepiece unit 21, the receiving unit 51 receives a scope ID from the storing unit 22. For example, the storing unit 22 may be configured by a radio frequency identifier (RFID) tag and the receiving unit 51 may be configured by an RFID detection circuit.

The imaging unit 52 is a portion that captures an object image condensed by the insertion unit 2 and generates a captured image. The imaging unit 52 includes, as illustrated in FIG. 2, a lens unit 521, a diaphragm 522, an image sensor 523, and a signal processing unit 524.

The lens unit 521 includes a focus lens 5211 (FIG. 2), takes in the object image condensed by the insertion unit 2, and forms the object image on an imaging surface of the image sensor 523.

The focus lens 5211 is configured using one or a plurality of lenses and moves along an optical axis to thereby adjust a focus position.

In the lens unit 521, a focus mechanism (not illustrated) that moves the focus lens 5211 along the optical axis is provided.

The diaphragm 522 is provided between the lens unit 521 and the image sensor 523 and adjusts, under the control by the control device 9, a light amount of the object image transmitted from the lens unit 521 to the image sensor 523.

In AF processing and remote shooting control explained below executed by the control device 9, the driving unit 54 causes the focus mechanism to operate and adjusts the focus position under the control by the control device 9. The driving unit 54 causes the diaphragm 522 to operate and adjusts a diaphragm value of the diaphragm 522 under the control by the control device 9.

The detecting unit 55 includes a position sensor such as a photo-interrupter and detects a position of the focus lens 5211 (hereinafter described as focusing position) at a present point in time. The detecting unit 55 outputs a signal corresponding to the detected focusing position to the control device 9. Further, the detecting unit 55 includes a linear encoder and the like and detects a diaphragm value of the diaphragm 522 at the present point in time. The detecting unit 55 outputs a signal corresponding to the detected diaphragm value to the control device 9.

The image sensor 523 is configured by an image sensor that receives the object image formed by the lens unit 521 and generates a captured image (an analog signal).

The signal processing unit 524 performs signal processing on the captured image (the analog signal) generated by the image sensor 523.

For example, the signal processing unit 524 performs, on the captured image (the analog signal) generated by the image sensor 523, signal processing such as processing for removing reset noise, processing for multiplying the analog signal by an analog gain for amplifying the analog signal, and A/D conversion.

The communication unit 53 is an interface that performs communication with the control device 9. The communication unit 53 transmits the captured image (a digital signal) subjected to the signal processing by the signal processing unit 524 and the scope ID received by the receiving unit 51 to the control device 9 and receives a control signal from the control device 9.

Configuration of the Control Device

The configuration of the control device 9 is explained with reference to FIG. 2.

The control device 9 includes, as illustrated in FIG. 2, a communication unit 91, an observation-image generating unit 92, a control unit 93, and a storing unit 94.

The communication unit 91 is equivalent to a first acquiring unit according to the present disclosure. The communication unit 91 is an interface that performs communication with the camera head 5 (the communication unit 53). The communication unit 91 receives the captured image (the digital signal) and the scope ID output from the communication unit 53 and transmits a control signal from the control unit 93.

The observation-image generating unit 92 processes, under the control by the control unit 93, the captured image (the digital signal) output from the camera head 5 and received by the communication unit 91. The observation-image generating unit 92 generates a video signal for display for displaying the captured image after being processed and outputs the video signal to the display device 7. The observation-image generating unit 92 includes, as illustrated in FIG. 2, an image processing unit 921 and a display controller 922.

The image processing unit 921 executes image processing and detection processing on the captured image (the digital signal) received by the communication unit 91.

Specifically, as the image processing, digital gain processing for multiplying the captured image (the digital signal) by a digital gain for amplifying the digital signal, optical black subtraction processing, white balance (WB) adjustment processing, demosaic processing, color matrix arithmetic processing, gamma correction processing, YC conversion processing for generating a luminance signal and a color difference signal (Y, Cb/Cr signal), expansion processing (electronic zoom), and the like may be illustrated.

The detection processing is processing for executing, based on pixel information (for example, a Y value (a luminance signal (a Y signal)) for each of pixels in a specific detection region Ar (see FIGS. 4B and 5B) in an entire image region in the captured image after the image processing explained above is executed, detection of contrast and a frequency component of an image in the detection region Ar, detection of a luminance average and maximum and minimum pixels in the detection region Ar by a filter or the like, comparison determination with a threshold, and detection of a histogram or the like. The detection region Ar is a rectangular region centering on an image center of the captured image (see FIGS. 4B and 5B). Note that the detection region Ar is not limited to the region located in the image center of the captured image. A region located in another position may be adopted as the detection region Ar. The image processing unit 921 outputs detection information (the contrast, the frequency component, the luminance average, the maximum and minimum pixels, the histogram, and the like) obtained by the detection processing to the control device 9.

The display controller 922 generates a video signal for display for displaying the captured image (the luminance signal and the color difference signal (the Y, Cb/Cr signal)) after the image processing is executed by the image processing unit 921. The display controller 922 outputs the video signal to the display device 7.

The control unit 93 is configured by, for example, a CPU, an FPGA, or the like and controls the operations of the imaging unit 52, the light source device 3, and the display device 7 and controls the operation of the entire control device 9. The control unit 93 has functions of a focus controller, a second acquiring unit, an object-distance calculating unit, a brightness adjustment unit, and a motion-amount calculating unit according to the present disclosure. Note that the functions are explained in "operation of the control device" below.

The storing unit 94 stores a program to be executed by the control unit 93, information necessary for processing of the control unit 93, and the like. As the information necessary for the processing of the control unit 93, an ID conversion table may be illustrated.

The ID conversion table is a table in which, for each of scope IDs different from one another, a hyperfocal distance corresponding to the insertion unit 2 having the scope ID and range information corresponding to the insertion unit 2 and indicating a range of an object distance from the distal end of the insertion unit 2 to the object at which remote shooting is performed are set. In the first embodiment, as the range information, a minimum value of the object distance at which the remote shooting is performed is adopted. That is, if the object distance is equal to or larger than the minimum value, the control unit 93 may determine that the remote shooting is performed.

Operation of the Control Device

The operation of the control device 9 explained above is explained.

Figure 3:
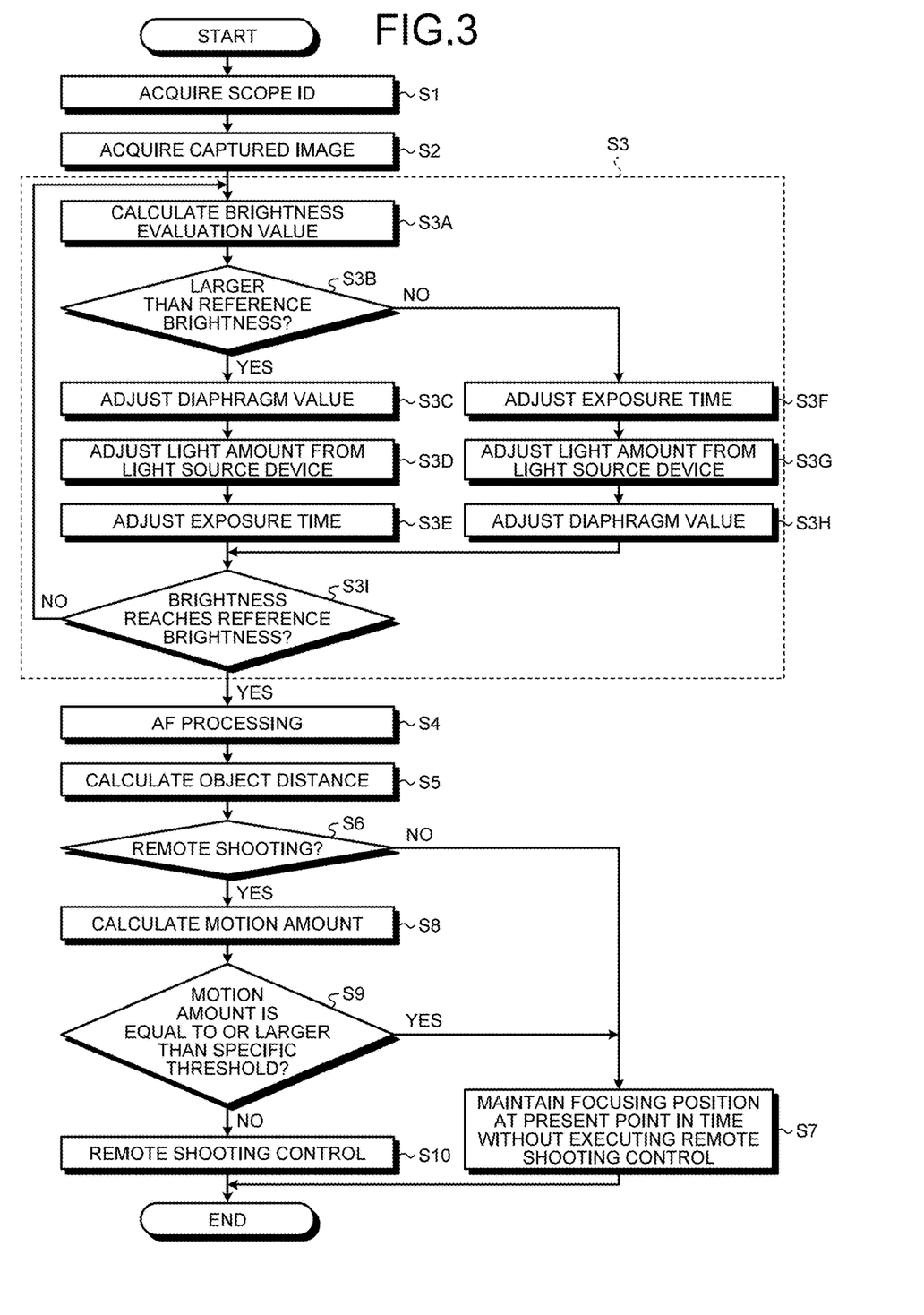
FIG. 3 is a flowchart illustrating the operation of a control device.

FIG. 3 is a flowchart illustrating the operation of the control device 9.

First, the control unit 93 acquires, via the communication unit 91, a scope ID received by the receiving unit 51 (step S1).

After step S1, the control unit 93 drives the light source device 3. Consequently, light emitted from the light source device 3 is radiated on an object from the distal end of the insertion unit 2. The control unit 93 causes the image sensor 523 to capture, at a predetermined frame rate, an object image radiated on the object and reflected by the object. The imaging unit 52 captures the object image and sequentially generates captured images. Consequently, the communication unit 91 sequentially receives the captured images from the camera head 5 (step S2).

After step S2, the control unit 93 executes brightness adjustment processing as explained below (step S3).

First, the control unit 93 calculates, based on detection information (a luminance average) obtained by the detection processing of the image processing unit 921 for the captured image, a brightness evaluation values for changing brightness of an image in the detection region Ar in the entire image region in the captured image to reference brightness (changing the detection information (the luminance average) to a reference luminance average) (step S3A). As the brightness evaluation value, first to fifth brightness evaluation values explained below may be illustrated.

The first brightness evaluation value is a diaphragm value of the diaphragm 522.

The second brightness evaluation value is a light amount of light supplied by the light source device 3.

The third brightness evaluation value is an exposure time (an electronic shutter) of pixels in the image sensor 523.

After step S3A, when the brightness of the image in the detection region Ar is larger than the reference brightness (step S3B: Yes), the control unit 93 outputs a control signal to the camera head 5 (the driving unit 54), sets the diaphragm value of the diaphragm 522 to the first brightness evaluation value calculated in step S3A and increases the diaphragm value (step S3C). That is, the control unit 93 narrows the diaphragm 522. After step S3C, the control unit 93 outputs a control signal to the light source device 3, sets the light amount of the light supplied by the light source device 3 to the second brightness evaluation value calculated in step S3A, and reduces the light amount (step S3D). After step S3D, the control unit 93 outputs a control signal to the camera head 5 (the driving unit 54), sets the exposure time of the pixels of the image sensor 523 to the third brightness evaluation value calculated in step S3A, and reduces the exposure time (step S3E).

On the other hand, when the brightness of the image in the detection region Ar is lower than the reference brightness (step S3B: No), the control unit 93 outputs a control signal to the camera head 5 (the driving unit 54), sets the exposure time of the pixels of the image sensor 523 to the third brightness evaluation value calculated in step S3A, and increases the exposure time (step S3F). After step S3F, the control unit 93 outputs a control signal to the light source device 3, sets the light amount of the light supplied by the light source device 3 to the second brightness evaluation value calculated in step S3A, and increases the light amount (step S3G). After step S3G, the control unit 93 outputs a control signal to the camera head 5 (the driving unit 54), sets the diaphragm value of the diaphragm 522 to the first brightness evaluation value calculated in step S3A, and reduces the diaphragm value (step S3H). That is, the control unit 93 opens the diaphragm 522.

When the brightness of the image in the detection region Ar does not reach the reference brightness (step S3I: No), the control unit 93 returns to step S3A and repeats the processing in steps S3A to S3I until the brightness of the image reaches the reference brightness (step S3I: Yes).

After step S3 (when it is determined "Yes" in step S3I), the control unit 93 executes AF processing as explained below (step S4).

Specifically, in step S4, the control unit 93 calculates, based on the detection information (the contrast and the frequency component) obtained by the detection processing of the image processing unit 921 for the captured image, a focus evaluation value for evaluating a focus state of the image in the detection region Ar in the entire image region in the captured image. For example, the control unit 93 sets, as the focus evaluation value, the contrast obtained by the detection processing of the image processing unit 921 or a sum of high frequency components in the frequency component obtained by the detection processing. Note that a larger value of the focus evaluation value indicates that the image is more focused. The control unit 93 controls the operation of the driving unit 54 with a hill-climbing method based on the calculated focus evaluation value and the focusing position at the present point in time detected by the detecting unit 55 to move the focus lens 5211 such that the image in the detection region Ar in the entire image region in the captured image changes to the focus state.

After step S4, the control unit 93 calculates, based on the focusing position at the present point in time detected by the detecting unit 55, an object distance WD (see FIGS. 4A and 5A) from the distal end of the insertion unit 2 to an object 100 (see FIGS. 4A and 5A) (step S5).

Incidentally, a separation distance between the focusing position and a disposition position of the image sensor 523 has a correlation with the object distance. For example, when the separation distance is relatively small, the object distance is relatively large. On the other hand, when the separation distance is relatively large, the object distance is relatively small. Therefore, the control unit 93 calculates the object distance WD based on the separation distance.

Figure 4A:
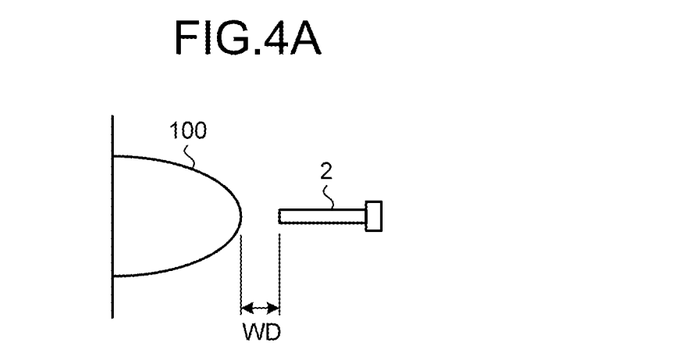
FIG. 4A is a diagram illustrating a state of proximity shooting.
Figure 4B:
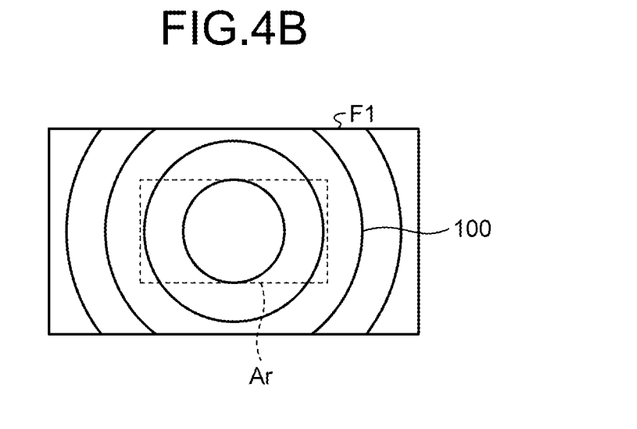
FIG. 4B is a diagram illustrating a captured image obtained by imaging an object in the proximity shooting.
Figure 5A:
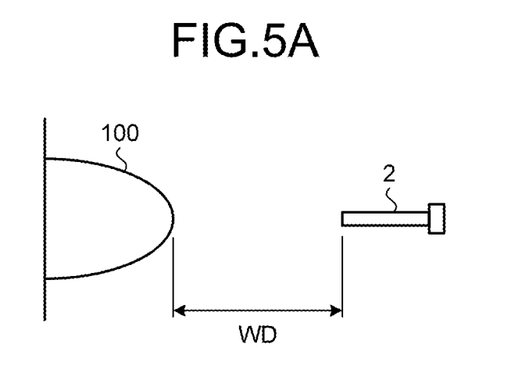
FIG. 5A is a diagram illustrating a state of remote shooting.
Figure 5B:
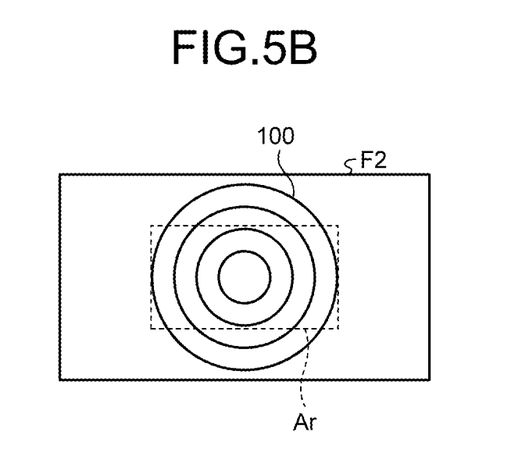
FIG. 5B is a diagram illustrating a captured image obtained by imaging an object in the remote shooting.

FIG. 4A is a diagram illustrating a state of proximity shooting. FIG. 4B is a diagram illustrating a captured image F1 obtained by imaging the object 100 in the proximity shooting. FIG. 5A is a diagram illustrating a state of remote shooting. FIG. 5B is a diagram illustrating a captured image F2 obtained by imaging the object 100 in the remote shooting.

After step S5, the control unit 93 determines, based on the object distance WD calculated in step S5, whether a shooting state at the present point in time is the remote shooting (step S6).

Incidentally, the proximity shooting means shooting in a state in which the object distance WD is relatively small as illustrated in FIG. 4A. On the other hand, as illustrated in FIG. 5A, the remote shooting means shooting in a state in which the object distance WD is relatively large.

Specifically, in step S6, the control unit 93 refers to the ID conversion table stored in the storing unit 94 and recognizes the range information corresponding to the scope ID acquired in step S1 (in the first embodiment, a minimum value of the object distance at which the remote shooting is performed). When the object distance WD calculated in step S5 is equal to or larger than the minimum value (within a range based on the range information), the control unit 93 determines that the shooting state at the present point in time is the remote shooting. On the other hand, when the object distance WD calculated in step S5 is smaller than the minimum value, the control unit 93 determines that the shooting state at the present point in time is not the remote shooting.

When determining that the shooting state at the present point in time is not the remote shooting (step S6: No), the control unit 93 maintains the focusing position at the present point in time without executing remote shooting control explained below (step S7).

On the other hand, when determining that the shooting state at the present point in time is the remote shooting (step S6: Yes), the control unit 93 calculates, with a publicly-known method (for example, a block matching method or a gradient method), a motion amount from a captured image obtained before the captured image at the present point in time in time series to the captured image at the present point in time (step S8).

After step S8, the control unit 93 determines whether the motion amount calculated in step S8 is equal to or larger than a specific threshold (step S9).

When determining that the motion amount is equal to or larger than the specific threshold (step S9: Yes), the control unit 93 shifts to step S7.

On the other hand, when determining that the motion amount is smaller than the specific threshold (step S9: No), the control unit 93 executes remote shooting control explained below (step S10).

Specifically, in step S10, the control unit 93 refers to the ID conversion table stored in the storing unit 94 and recognizes a hyperfocal distance corresponding to the scope ID acquired in step S1. The control unit 93 outputs a control signal to the camera head 5 (the driving unit 54), changes the focusing position, and sets a focus position PP (see FIG. 6A) in a position of the hyperfocal distance.

Figure 6A:
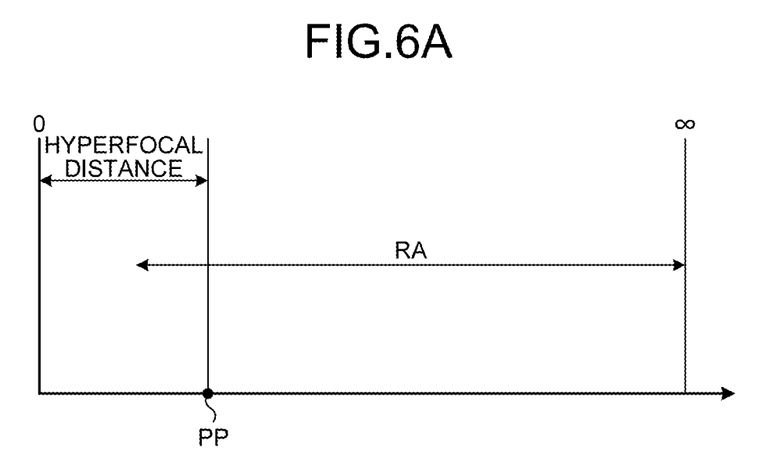
FIG. 6A is a diagram for explaining a hyperfocal distance.
Figure 6B:
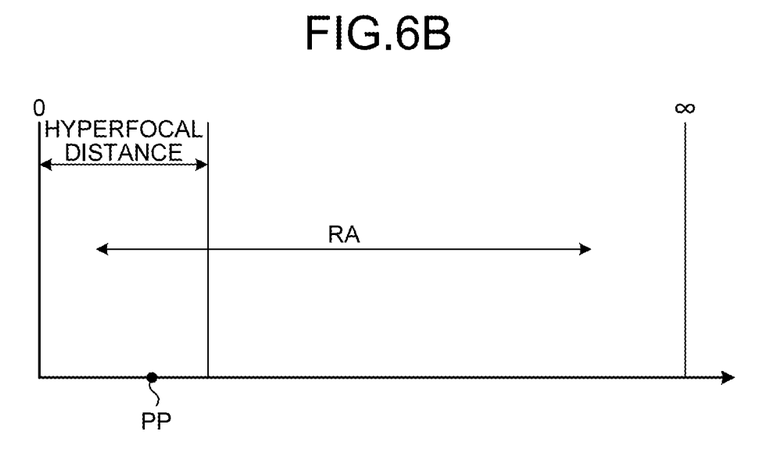
FIG. 6B is a diagram for explaining the hyperfocal distance.
Figure 6C:
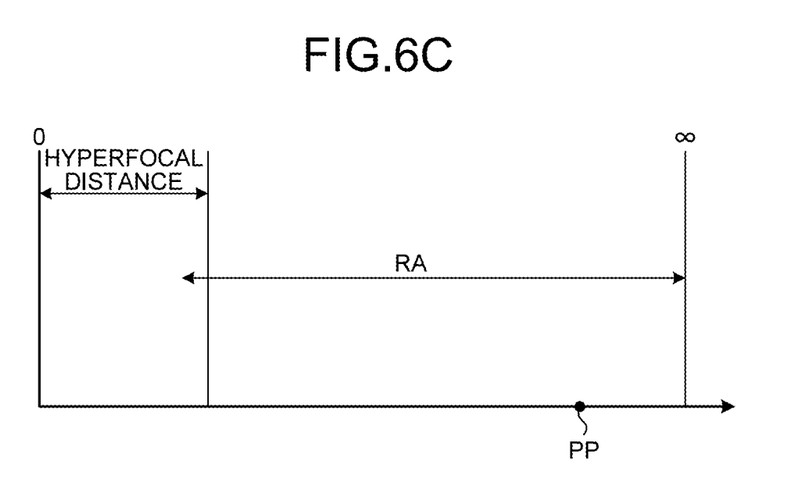
FIG. 6C is a diagram for explaining the hyperfocal distance.

FIGS. 6A to 6C are diagrams for explaining the hyperfocal distance. Note that, in FIGS. 6A to 6C, the horizontal axis indicates a distance from the image sensor 523 to an object side. In FIGS. 6A to 6C, a sign "RA" indicates a range in the focus state.

For example, when the focusing position is adjusted such that the focus position PP is further on the near side than the position of the hyperfocal distance, a distance is blurred as illustrated in a range RA in the focus state illustrated in FIG. 6B. On the other hand, when the focusing position is adjusted such that the focus position PP is further on the inner side than the position of the hyperfocal distance, a vicinity is blurred as illustrated in the range RA in the focus state illustrated in FIG. 6C. When step S10 is executed, as illustrated in FIG. 6A, the range RA in the focus state is from the vicinity to the distance (infinity) and a depth of field increases.

According to the first embodiment explained above, the following effects are achieved.

The control device 9 according to the first embodiment acquires the scope ID of the insertion unit 2. The control device 9 refers to the ID conversion table and acquires the hyperfocal distance corresponding to the insertion unit 2 having the scope ID and the range information indicating the range of the object distance at which the remote shooting is performed. Further, the control device 9 calculates the object distance WD based on the focusing position at the present point in time. When the object distance WD is included in the range based on the range information, the control device 9 executes the remote shooting control for moving the focus lens 5211 and setting the focus position PP in the position of the hyperfocal distance.

Therefore, with the control device 9 according to this embodiment, even in the case of the remote shooting, it is possible to obtain a captured image having a large depth of field and suitable for observation.

Incidentally, when the insertion unit 2 is pushed and pulled to be moved in the organism or when the insertion unit 2 is moved to the left and the right, a shooting state is not decided yet. That is, even if the remote shooting is performed at present point in time, the shooting state sometimes shifts to the proximity shooting or the like according to the movement of the insertion unit 2. Accordingly, even if the remote shooting is performed at the present point in time, it is meaningless to execute the remote shooting control in the case described above.

Therefore, the control device 9 according to this embodiment determines the case described above according to a motion amount of the captured image and, when the motion amount is equal to or larger than a specific threshold, does not execute the remote shooting control. Accordingly, it is possible to avoid unnecessarily moving the focusing position.

Second Embodiment

A second embodiment is explained.

In the following explanation, the same components as the components in the first embodiment explained above are denoted by the same reference numerals and signs. Detailed explanation of the components is omitted or simplified.

Figure 7:
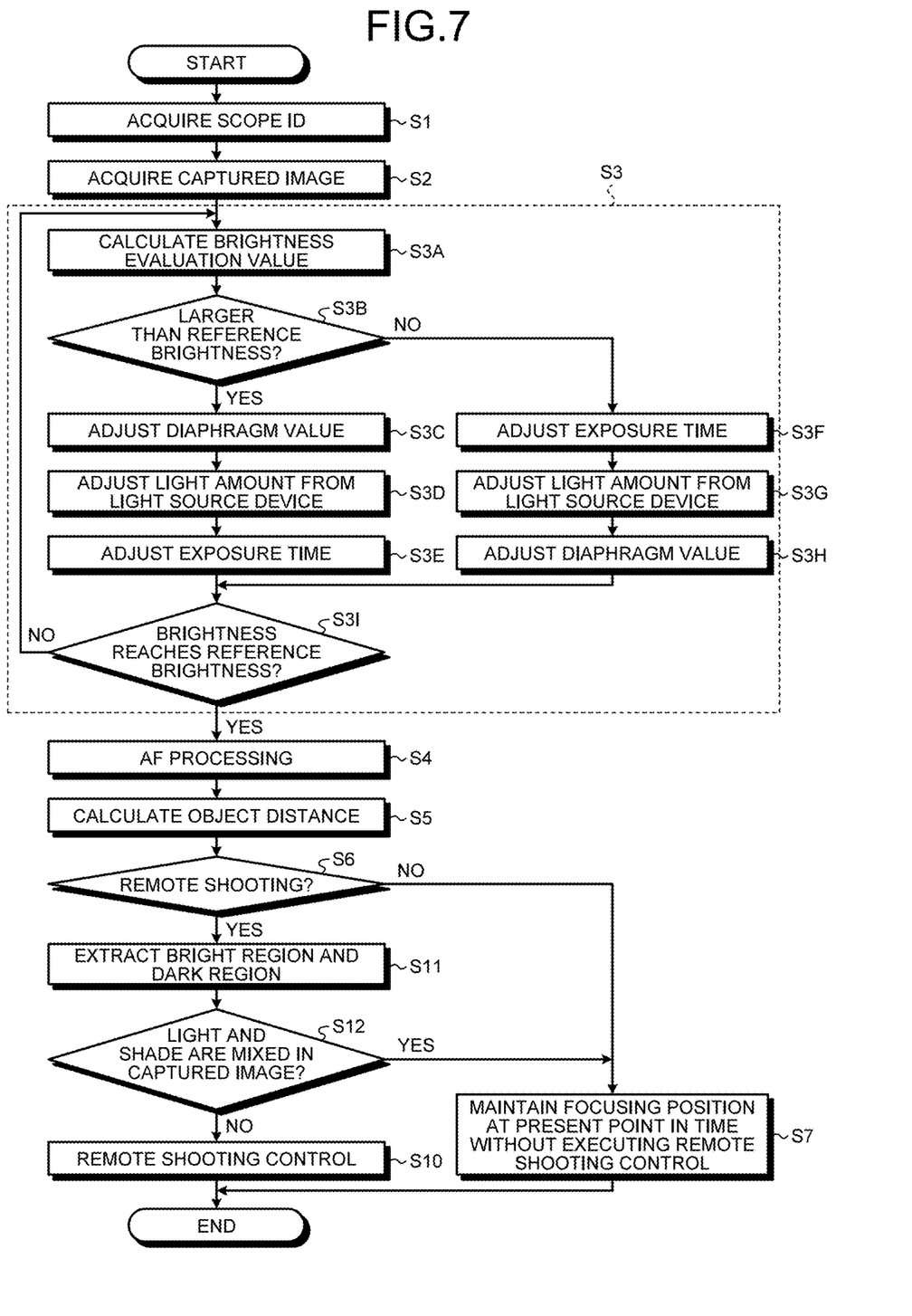
FIG. 7 is a flowchart illustrating the operation of a control device according to a second embodiment.

FIG. 7 is a flowchart illustrating the operation of the control device 9 according to the second embodiment.

As illustrated in FIG. 7, the control device 9 according to the second embodiment performs an operation different from the operation explained in the first embodiment above.

In the operation of the control device 9 according to the second embodiment, as illustrated in FIG. 7, steps S11 and S12 are adopted instead of steps S8 and S9 explained in the first embodiment. Steps S11 and S12 are mainly explained below.

When determining that the shooting state at the present point in time is the remote shooting (step S6: Yes), the control unit 93 extracts a bright region and a dark region in the captured image (step S11).

Specifically, in step S11, the control unit 93 extracts a bright region formed by pixels, a pixel level of which is equal to or larger than a first threshold, and having a size (the number of pixels) equal to or larger than a second threshold in the detection region Ar of the captured image. As the pixel level, a luminance value and an RGB value (a pixel value) corresponding to a Y signal (a luminance signal) may be illustrated. In the second embodiment, the luminance value is adopted as the pixel level. The control unit 93 extracts a dark region formed by pixels, a pixel level of which is equal to or smaller than a third threshold smaller than the first threshold, and having a size (the number of pixels) equal to or larger than a fourth threshold in the detection region Ar of the captured image. That is, in the control unit 93 according to the second embodiment, the function of the motion-amount calculating unit according to the present disclosure is omitted and functions of a bright-region extracting unit and a dark-region extracting unit according to the present disclosure are added.

After step S11, the control unit 93 determines whether light and shade are mixed in the detection region Ar of the captured image (step S12).

Specifically, in step S12, when both of the bright region and the dark region are successfully extracted from the detection region Ar of the captured image in step S11, the control unit 93 determines that light and shade are mixed in the detection region Ar of the captured image. The control unit 93 shifts to step S7.

On the other hand, in step S12, when both of the bright region and the dark region are not successfully extracted from the detection region Ar of the captured image in step S11, the control unit 93 determines that light and shade are not mixed in the detection region Ar of the captured image. The control unit 93 shifts to step S10.

Figure 8A:
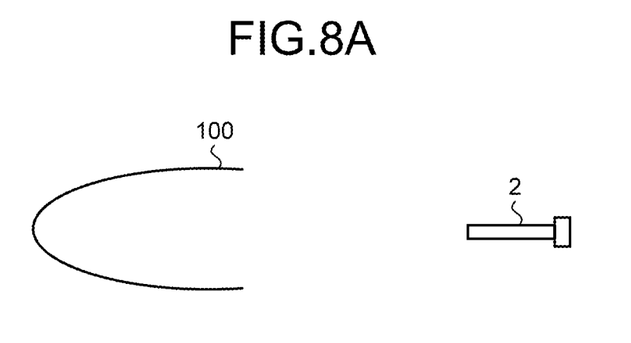
FIG. 8A is a diagram for explaining a case in which light and shade are mixed in a detection region of a captured image.
Figure 8B:
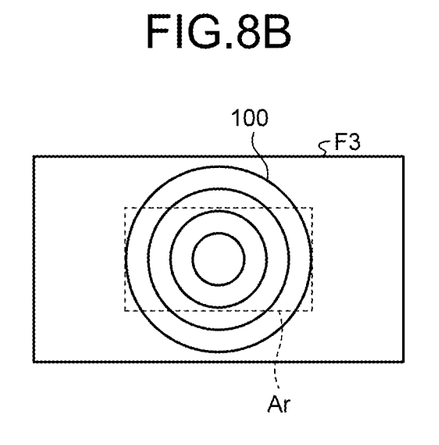
FIG. 8B is a diagram for explaining the case in which light and shade are mixed in the detection region of the captured image.
Figure 9A:
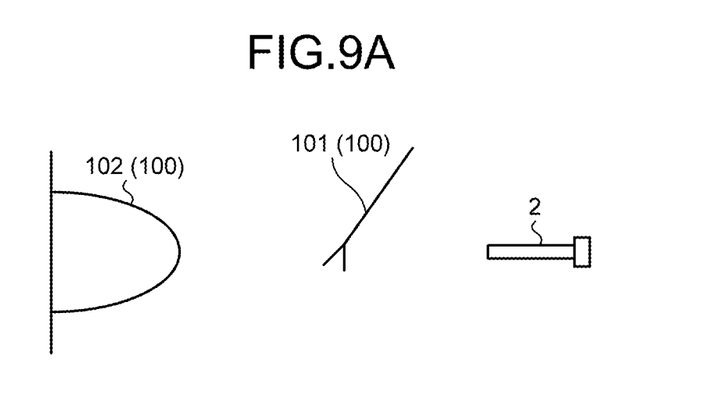
FIG. 9A is a diagram for explaining a case in which light and shade are mixed in a detection region of a captured image.
Figure 9B:
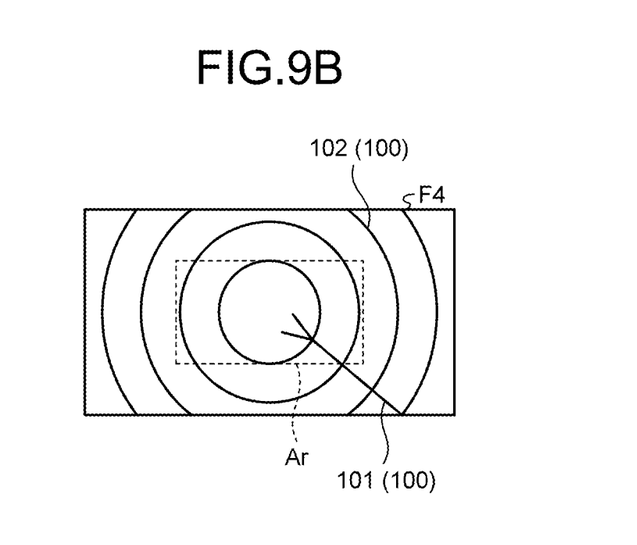
FIG. 9B is a diagram for explaining the case in which light and shade are mixed in the detection region of the captured image.

FIGS. 8A, 8B, 9A, and 9B are diagrams for explaining a case in which light and shade are mixed in the detection region Ar of the captured image. Specifically, FIG. 8A is a diagram illustrating a state in which the object 100 of a deep cavity is imaged. FIG. 8B is a diagram illustrating a captured image F3 captured in the state illustrated in FIG. 8A. FIG. 9A is a diagram illustrating a state in which the object 100, the near side of which is a pair of forceps 101 and the inner side of which is an organ 102, is imaged. FIG. 9B is a diagram illustrating a captured image F4 captured in the state illustrated in FIG. 9A.

Incidentally, as illustrated in FIG. 8A, when the object 100 of the deep cavity is imaged, the near side of the deep cavity is bright and the inner side of the deep cavity is dark. That is, light and shade are mixed in the detection region Ar of the captured image F3 obtained by imaging the object 100 of the deep cavity in this way.

As illustrated in FIG. 9A, when the object 100, the near side of which is the pair of forceps 101 and the inner side of which is the organ 102, is imaged, the pair of forceps 101 on the near side is bright and the organ 102 on the inner side is dark. That is, light and shade are mixed in the detection region Ar of the captured image F4 obtained by imaging the object 100, the near side of which is the pair of forceps 101 and the inner side of which is the organ 102 in this way.

According to the second embodiment explained above, the following effects are achieved other than the same effects as the effects in the first embodiment explained above.

Incidentally, when light and shade are mixed in the detection region Ar of the captured image, it is difficult to locate the focusing position in an appropriate position in AF processing. Accordingly, in this case, the object distance WD may not be appropriately calculated. The determination about whether the remote shooting is performed at the present point in time may not be accurately executed.

Therefore, the control device 9 according to this embodiment determines the case according to whether both of the bright region and the dark region are successfully extracted and, when both of the bright region and the dark region are successfully extracted, does not execute the remote shooting control. Accordingly, it is possible to avoid unnecessarily moving the focusing position.

OTHER EMBODIMENTS

The modes for carrying out the present disclosure are explained above. However, the present disclosure should not be limited by only the first and second embodiments explained above.

In the first and second embodiments explained above, the three adjustments, that is, the adjustment of the diaphragm value of the diaphragm 522, the adjustment of the light amount of the light source device 3, and the adjustment of the exposure time are explained as the brightness adjustment processing. However, the brightness adjustment processing is not limited to this. For example, as the brightness adjustment processing, adjustment of the analog gain multiplied by the signal processing unit 524 and adjustment of the digital gain multiplied by the image processing unit 921 may be adopted.

In the first and second embodiments explained above, the control device 9 refers to the ID conversion table and acquires the hyperfocal distance corresponding to the insertion unit 2 having the scope ID. However, the control device 9 is not limited to this and may calculate the hyperfocal distance.

For example, the hyperfocal distance is represented by the following Expression (1).

Specifically, the ID conversion table according to this modification is a table in which, for each of scope IDs different from one another, a focal length and a permission circle of confusion corresponding to the insertion unit 2 having the scope ID and range information corresponding to the insertion unit 2 are set. In step S10, the control device 9 refers to the ID conversion table and acquires the focal length and the permission circle of confusion corresponding to the insertion unit 2 having the scope ID. The control device 9 acquires a diaphragm value at the present point in time after the brightness adjustment processing is executed. The control device 9 substitutes the acquired focal length, the acquired permission circle of confusion, and the acquired diaphragm value in the following Expression (1) to calculate the hyperfocal distance.

$$\text{hyperfocal distance (mm)} = \text{focal length (mm)} \times \text{focal length} \quad (1)$$
$$\text{(mm)} \div \text{diaphragm value} \div \text{permission circle of confusion (mm)}$$

In the first and second embodiments explained above, in the flow illustrated in FIG. 3, the order of the processing may be changed in a range without contradiction. The techniques described in the first and second embodiments may be combined as appropriate.

Note that configurations explained below also belong to the technical scope of the present disclosure.

With the medical control device and the medical observation system according to the present disclosure, it is possible to obtain a captured image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control device comprising
a focus controller configured to
move a focus lens included in an imaging device configured to capture an object image taken in by an endoscope and generate a captured image, and
control a focus position, wherein
the focus controller is configured to execute remote shooting control for moving the focus lens and setting the focus position in a position of a hyperfocal distance corresponding to the endoscope in a case where an object distance from the endoscope to an object is included in a range of an object distance from the endoscope to the object at which remote shooting is performed, and
a motion-amount calculator configured to calculate a motion amount from the captured image preceding in time series to the captured image following in time series, wherein
the focus controller is configured not to execute the remote shooting control in a case where the motion amount is equal to or larger than a specific threshold.

2. The medical control device according to claim 1, further comprising:
first acquiring circuitry configured to acquire identification information of the endoscope; and
second acquiring circuitry configured to acquire, based on the identification information, the hyperfocal distance corresponding to the endoscope and range information corresponding to the endoscope and indicating the range of the object distance from the endoscope to the object at which the remote shooting is performed, wherein
the focus controller is configured to execute the remote shooting control for moving the focus lens and setting the focus position in the position of the hyperfocal distance in a case where the object distance from the endoscope to the object is included in a range based on the range information.

3. The medical control device according to claim 1, further comprising an object-distance calculator configured to calculate the object distance from the endoscope to the object based on a position of the focus lens.

4. The medical control device according to claim 1, further comprising brightness adjuster configured to control an operation of a diaphragm included in the imaging device and adjust brightness of the captured image.

5. The medical control device according to claim 1, further comprising:
a bright-region extracting circuit including first pixels in the captured image, a pixel level of each of the first pixels being equal to or larger than a first threshold, the bright-region extracting circuit being configured to extract a bright region having a size equal to or larger than a second threshold; and
a dark-region extracting circuit including second pixels in the captured image, a pixel level of the second pixels being equal to or smaller than a third threshold smaller than the first threshold, the dark-region extracting circuit being configured to extract a dark region having a size equal to or larger than a fourth threshold, wherein
the focus controller is configured not to execute the remote shooting control in a case where both of the bright region and the dark region are extracted by the bright-region extracting circuit and the dark-region extracting circuit from the captured image.

6. A medical observation system comprising:
an endoscope configured to take in an object image;
an imaging device configured to capture the object image taken in by the endoscope and generate a captured image; and
a medical control device configured to control an operation of the imaging device, the medical control device including
a focus controller configured to move a focus lens included in the imaging device and control a focus position, wherein
the focus controller is configured to execute remote shooting control for moving the focus lens and setting the focus position in a position of a hyperfocal distance corresponding to the endoscope in a case where an object distance from the endoscope to an object is included in a range of an object distance from the endoscope to the object at which remote shooting is performed; and
a motion-amount calculator configured to calculate a motion amount from the captured image preceding in time series to the captured image following in time series, wherein
the focus controller is configured not to execute the remote shooting control in a case where the motion amount is equal to or larger than a specific threshold.

7. The medical observation system according to claim 6, wherein the medical control device further includes:
a bright-region extracting circuit including first pixels in the captured image, a pixel level of each of the first pixels being equal to or larger than a first threshold, the bright-region extracting circuit being configured to extract a bright region having a size equal to or larger than a second threshold; and
a dark-region extracting circuit including second pixels in the captured image, a pixel level of the second pixels being equal to or smaller than a third threshold smaller than the first threshold, the dark-region extracting circuit being configured to extract a dark region having a size equal to or larger than a fourth threshold, wherein
the focus controller is configured not to execute the remote shooting control in a case where both of the bright region and the dark region are extracted by the bright-region extracting circuit and the dark-region extracting circuit from the captured image.

8. A medical control device comprising
a focus controller configured to
move a focus lens included in an imaging device configured to capture an object image taken in by an endoscope and generate a captured image, and
control a focus position, wherein
the focus controller is configured to execute remote shooting control for moving the focus lens and setting the focus position in a position of a hyperfocal distance corresponding to the endoscope in a case where an object distance from the endoscope to an object is included in a range of an object distance from the endoscope to the object at which remote shooting is performed;
a bright-region extracting circuit including first pixels in the captured image, a pixel level of each of the first pixels being equal to or larger than a first threshold, the bright-region extracting circuit being configured to extract a bright region having a size equal to or larger than a second threshold; and
a dark-region extracting circuit including second pixels in the captured image, a pixel level of the second pixels being equal to or smaller than a third threshold smaller than the first threshold, the dark-region extracting circuit being configured to extract a dark region having a size equal to or larger than a fourth threshold, wherein
the focus controller is configured not to execute the remote shooting control in a case where both of the bright region and the dark region are extracted by the bright-region extracting circuit and the dark-region extracting circuit from the captured image.

9. The medical control device according to claim 8, further comprising a brightness adjuster configured to control an operation of a diaphragm included in the imaging device and adjust brightness of the captured image before the bright-region extracting circuit extracts the bright region and the dark-region extracting circuit extracts the dark region.

10. A medical control method comprising
moving a focus lens included in an image sensor configured to capture an object image taken by a medical imager and generate a captured image;
controlling a focus position of the focus lens;
executing remote shooting control for moving the focus lens and setting the focus position in a position of a hyperfocal distance corresponding to the medical imager in a case where an object distance from the medical imager to an object is included in a range of an object distance from the medical imager to the object at which remote shooting is performed;
determining a motion amount from the captured image preceding in time series to the captured image following in time series, or whether light and shade are mixed in the captured image; and
not executing remote shooting control on condition that the motion amount is equal to or larger than a specific threshold, or
light and shade are mixed in the captured image.

11. The medical control method according to claim 10, further comprising determining that light and shade are mixed in the captured image on condition that
a bright region of first pixels each having a pixel level equal to or larger than a first threshold has a size equal to or larger than a second threshold, and a dark region of second pixels each having a pixel level equal to or smaller than a third threshold, less than the first threshold, has a size equal to or larger than a fourth threshold.

12. The medical control method according to claim 10, further comprising controlling a diaphragm in the medical imager and adjusting brightness of the captured image before determining the motion amount or whether the light and shade are mixed in the captured image.

\* \* \* \* \*